US009285262B2

(12) United States Patent
Kneubuehl et al.

(10) Patent No.: US 9,285,262 B2
(45) Date of Patent: Mar. 15, 2016

(54) SYSTEM FOR MANAGING BULK LIQUIDS AND/OR SOLIDS

(71) Applicant: Roche Diagnostics Operations, Inc., Indianapolis, IN (US)

(72) Inventors: Daniel Kneubuehl, Kerzers (CH); Martin Lustenberger, Villars sur Glâne (CH); Christian Marty, Goldau (CH); Emanuel Masel, Cressier (CH); André Peter, Meggen (CH); Markus Troxler, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 186 days.

(21) Appl. No.: 14/103,992

(22) Filed: Dec. 12, 2013

(65) Prior Publication Data

US 2014/0174837 A1    Jun. 26, 2014

(30) Foreign Application Priority Data

Dec. 20, 2012 (EP) .................................... 12198647

(51) Int. Cl.
*G01G 17/04* (2006.01)
*G01N 35/10* (2006.01)
(Continued)

(52) U.S. Cl.
CPC ............... *G01G 15/006* (2013.01); *G01G 3/16* (2013.01); *G01G 17/04* (2013.01); *G01N 35/1002* (2013.01); *G01N 2035/00217* (2013.01)

(58) Field of Classification Search
CPC ............ G01F 23/20; G01G 3/08; G01G 3/16; G01G 15/006; G01G 17/04; G01N 2035/00217; G01N 35/1002; G01L 1/10

USPC ................................................. 73/296, 290 V
See application file for complete search history.

(56) References Cited

U.S. PATENT DOCUMENTS 2,330,857 A * 10/1943 Alcott ............................. 177/45
4,382,478 A * 5/1983 Hearn ............................ 177/169
(Continued)

FOREIGN PATENT DOCUMENTS

EP    0558212 A2    9/1993
EP    1832879 A2    9/2007
(Continued)

OTHER PUBLICATIONS

Rouff, Marc et al., "Control of mechanical oscillators and their application to weight and force measurement," Mechatronics, Aug. 1993, pp. 399-407, vol. 3, No. 4.

*Primary Examiner* — Randy W Gibson
(74) *Attorney, Agent, or Firm* — Roche Diagnostics Operations, Inc.

(57) ABSTRACT

A system for managing of bulk liquids and/or bulk solids for in-vitro diagnostics is disclosed. The system comprises a sample processing unit and a container unit for receiving a supply container supplying the sample processing unit with a bulk liquid/solid and/or a waste container receiving waste from the sample processing unit. The system further comprises a weight measuring device comprising a loading plate, a base and a force measuring cell. The force measuring cell comprises a sensor comprising a tensioned sensor wire. The loading plate is biased with respect to the base by a weight applied to the loading plate by a container and to transfer force to the force measuring cell. The transferred force causes a deformation of the force measuring cell and a change in tension of the sensor wire causing a change in vibrational frequency resulting in a signal indicative of the weight of the container.

15 Claims, 6 Drawing Sheets

(51) Int. Cl.
*G01F 23/20* (2006.01)
*G01G 15/00* (2006.01)
*G01G 3/16* (2006.01)
*G01N 35/00* (2006.01)

(56) References Cited

U.S. PATENT DOCUMENTS

| | | | |
|---|---|---|---|
| 4,458,539 A * | 7/1984 | Bilstad et al. | 73/861 |
| 4,478,303 A * | 10/1984 | Boyles | 177/210 FP |
| 4,614,245 A * | 9/1986 | Yamanaka | 177/210 FP |
| 4,815,547 A * | 3/1989 | Dillon et al. | 177/25.14 |
| 5,088,334 A | 2/1992 | Wirth | |
| 5,095,764 A * | 3/1992 | Saner | 73/862.59 |
| 5,555,764 A * | 9/1996 | Dybas | 73/296 |
| 5,623,128 A | 4/1997 | Grimm et al. | 177/25.13 |
| 5,802,859 A * | 9/1998 | Zugibe | 62/125 |
| 6,327,913 B1 | 12/2001 | Lustenberger et al. | |
| 6,954,966 B2 * | 10/2005 | Shimizu et al. | 15/319 |
| 6,968,805 B1 * | 11/2005 | Rathbun | 116/227 |
| 6,978,671 B1 * | 12/2005 | Meggs et al. | 73/149 |
| 7,737,372 B2 * | 6/2010 | Dougherty et al. | 177/245 |
| 7,770,448 B2 * | 8/2010 | Misra et al. | 73/296 |
| 8,141,420 B2 * | 3/2012 | Hirao | 73/198 |
| 2003/0047178 A1 * | 3/2003 | Barth et al. | 126/41 R |
| 2006/0134598 A1 * | 6/2006 | Kenney | 435/3 |
| 2007/0212261 A1 * | 9/2007 | Tanaka et al. | 422/67 |
| 2010/0104478 A1 * | 4/2010 | Kondou | 422/100 |
| 2010/0247379 A1 * | 9/2010 | Schmidt | 422/67 |
| 2014/0182396 A1 * | 7/2014 | Okoba | 73/863.01 |
| 2014/0311239 A1 * | 10/2014 | Marjanovic et al. | 73/296 |

FOREIGN PATENT DOCUMENTS

| | | |
|---|---|---|
| EP | 2216397 A1 | 8/2010 |
| FR | 2957676 A1 | 9/2011 |
| GB | 1526489 A | 9/1978 |
| GB | 2128329 A | 4/1984 |
| GB | 2251488 A | 7/1992 |

* cited by examiner

SYSTEM FOR MANAGING BULK LIQUIDS AND/OR SOLIDS

CROSS-REFERENCE TO RELATED APPLICATIONS

This application is a continuation of EP 12198647.5, filed Dec. 20, 2012, which is hereby incorporated by reference.

BACKGROUND

The present disclosure generally relates to a system for managing bulk liquids and/or bulk solids for in-vitro diagnostics.

In-vitro diagnostic assays are nowadays typically automated. A large number of diagnostic instruments are available, which may conduct different types of assays. Depending on throughput, these diagnostic instruments may consume large amounts of bulk supply liquids such as wash liquids, system liquids and reagents as well as a large amount of bulk supply solids, such as reaction vessels and disposable pipetting tips required for processing samples. On the other hand, the same diagnostic instruments may generate large amounts of bulk waste liquids such as samples, reagents, wash and system liquids, mixtures thereof, as well as bulk waste solids such as sample vessels, reaction vessels, reagent vessels, disposable tips used for processing samples. These bulk waste liquids and solids generate significant disposal problems due to possible contamination with various infectious diseases. As a result, rules and regulations for the handling and disposal of waste have been imposed by various governmental and regulatory agencies, requiring the use of automated controls to protect from exposure.

Various systems have been implemented in the field of in-vitro diagnostics for managing bulk liquids and bulk solids.

A technical problem encountered when automatically managing bulk liquids and/or bulk solids is the fill volume detection, that is the detection of the amount of bulk liquid or solid in a bulk container in order to determine at least when it is empty or nearly empty in the case of a bulk supply container and when it is full or nearly full in the case of a bulk waste container.

Commonly used sensors for fill volume detection are normally suitable only for specific applications, for example, only for bulk liquids. For example, several liquid level detectors are known. Some of these are invasive, requiring, for example, a probe such as a floating or immersed assembly, for example, an electrode. Invasive methods present major disadvantages for diagnostic applications. Invasive sensors are expensive, are dependent on the characteristics of the liquid such as chemical composition, conductivity, presence of foam, viscosity and temperature. They are also prone to chemical deposition and contamination and require cleaning and maintenance.

Other types of liquid level detectors, which are non-invasive, are also known, like for example acoustic or optical detectors. These detectors, however, depending on container type and material, may be difficult to position and to handle, they are more expensive, and may present issues with long-term stability and space requirements. The characteristics of the liquid such as the presence of foam may also affect the performance.

Gravimetric detectors to measure the weight of bulk containers are also known. These are however expensive, complex, large in size whereas the space in the instrument is typically limited, difficult to position and not reliable as they may be influenced by other elements coupled to the bulk containers.

Pressure detectors such as strain gauge detectors are also known. They suffer however from long-term stability and environmental factors such as humidity and temperature.

Also, both invasive and-non invasive detectors have a low applicability for continuous loading/unloading of bulk containers, i.e., during operation of the instrument.

Therefore, there is a need for a system for managing bulk liquids and/or bulk solids, which is cheap, compact, more accurate, more robust, more reproducible, more long-term stable, and less influenced by environmental and handling factors and that it is applicable for both bulk supply liquids and bulk supply solids, as well as for both bulk waste liquids and bulk waste solids so that the system is independent from the characteristics of a bulk liquid such as chemical composition, conductivity, presence of foam, viscosity and temperature.

SUMMARY

According to the present disclosure, a system for managing bulk liquids and/or bulk solids for in-vitro diagnostics is presented. The system can comprise a sample processing unit, at least one bulk container unit for receiving at least one bulk liquid and/or bulk solid supply container for supplying the sample processing unit with at least one bulk liquid and/or bulk solid respectively and/or at least one bulk liquid and/or bulk solid waste container for receiving at least one bulk liquid and/or bulk solid waste respectively from the sample processing unit, and at least one weight measuring device comprising a loading plate, a reference base and a force measuring cell connected to the loading plate and to the reference base. The force measuring cell can comprise a vibrating wire sensor comprising a tensioned sensor wire. The loading plate can be biased with respect to the reference base by a weight applied to the loading plate by a bulk container and to transfer force to the force measuring cell. The transferred force can cause a deformation of the force measuring cell and a change in tension of the sensor wire causing a change in vibrational frequency resulting in an electric signal indicative of the weight of the bulk container.

Accordingly, it is a feature of the embodiments of the present disclosure to provide a system for managing bulk liquids and/or bulk solids, which is cheap, compact, more accurate, more robust, more reproducible, more long-term stable, and less influenced by environmental and handling factors and that it is applicable for both bulk supply liquids and bulk supply solids, as well as for both bulk waste liquids and bulk waste solids so that the system is independent from the characteristics of a bulk liquid such as chemical composition, conductivity, presence of foam, viscosity and temperature. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The system can comprise a sample processing unit. The "sample processing unit" can be a stand-alone apparatus or a module within a larger instrument for in vitro diagnostics, such as, for example, for qualitative and/or quantitative evaluation of samples for diagnostic purpose, and/or for sorting and/or for preparation of samples before detection, or for storing and/or for disposal of samples after detection. In particular, a sample processing unit may be related to analytical and/or to pre-analytical and/or to post-analytical sample processing steps.

The term "sample", as used herein, can refer to a material suspected of containing an analyte of interest. The sample can be derived from any biological source, such as, for example a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as, for example, preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, such as, for example, after being diluted with another solution or after having being mixed with reagents, for example, to carry out one or more diagnostic assays like for example clinical chemistry assays, immunoassays, coagulation assays, nucleic acid testing, and the like. The term "sample" as used herein may therefore not only used for the original sample but can also relate to a sample which has already been processed (pipetted, diluted, mixed with reagents, enriched, having been purified, having been amplified, and the like. As used herein, the term "analyte" can refer to the compound or composition to be detected or measured in vitro for diagnostic purpose.

An example of a sample processing unit can be a "pre-analytical work cell", which can either be a standalone apparatus or module within a larger instrument for the sorting and/or preparation of samples before being processed by an analytical work cell. It may comprise for example one or more of the following: a resorting unit to sort samples according to type of in-vitro diagnostic test and/or priority of in-vitro diagnostic test, a centrifuge for centrifuging sample tubes, an aliquoting unit wherein a pipetting unit can be used to aliquot samples from sample tubes, a thermal treatment unit to subject the sample to a certain temperature, a separation unit to separate sample components, a sample dilution unit for diluting the sample with a diluting buffer or solvent, a reagent pipetting unit, for example, to prepare a sample for thermal treatment and/or in-vitro diagnostic test, and the like.

Another example of a sample processing unit can be an "analytical work cell", which can either be a stand-alone apparatus or module within a larger instrument for the detection, for example, qualitative and/or quantitative evaluation of samples for diagnostic purpose. An analytical work cell may comprise units for pipetting, dosing, mixing of samples and/or reagents. The analytical work cell may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. In particular, it may comprise one or more liquid processing units, such as a pipetting unit, to deliver samples and/or reagents to the reaction vessels. The pipetting unit may comprise a reusable washable needle, for example, a steel needle, or disposable pipette tips. The work cell may further comprise one or more mixing units, comprising, for example, a shaker to shake a cuvette or vessel comprising a liquid or a mixing paddle to mix liquids in a cuvette or reagent container. The analytical work cell may comprise a process and detection system whose workflow can be optimized for certain types of in-vitro diagnostic test. Examples of such work cells can be clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

Another example of a sample processing unit can be a "post-analytical work cell", which can either be a standalone apparatus or module within a larger instrument for the storing and/or disposal of samples after being processed by an analytical work cell. It may comprise, for example, a resorting unit to resort sample tubes, for example, to different storage racks and/or a refrigerated compartment.

Work-cells of the same or different type may be connected to each other and depend at least in part on each other, for example, each carrying out a dedicated task of a sample processing workflow, which may be a prerequisite before proceeding to another work-cell. Alternatively, work cells may work independently from each other, for example, each carrying out a separate task, for example, a different type of in-vitro diagnostic test on the same sample or different sample. In general, a work cell may comprise units for loading and/or unloading and/or transporting and/or storing sample tubes or racks comprising sample tubes or multi-well plates, units for loading and/or unloading and/or transporting and/or storing reagent containers or cassettes, units for loading and/or unloading and/or transporting and/or storing and/ or washing reaction vessels such as, for example, cuvettes, units for loading and/or unloading and/or transporting and/or storing pipette tips or tip racks. It may comprise identification units comprising sensors such as, for example, barcode or RFID readers. It may comprise wash stations for washing pipette tips or needles or reaction vessels, for example, cuvettes, mixing paddles, and the like.

The system can further comprise at least one bulk container unit for receiving at least one bulk container. The bulk container unit may be a module or compartment of the sample processing unit or it may be external to the sample processing unit and connected to the sample processing unit at least via bulk supply and/or waste lines.

A bulk container may be a bulk liquid and/or bulk solid supply container for supplying the sample processing unit with at least one bulk liquid and/or bulk solid respectively. The bulk container may be a bulk liquid and/or bulk solid waste container for receiving at least one bulk liquid and/or bulk solid waste respectively from the sample processing unit. A "bulk container" may be a container of any form and type depending on the bulk liquid or solid to be contained therein. It may have for example the form of a bottle, bin, cassette, rack or box and may be made, for example, of plastics, glass, paper or cardboard as long as it is suitable for containing a certain bulk liquid or solid. In particular, it may have a different size or capacity depending on the throughput of the sample processing unit in consuming bulk supply liquids and/or solids and/or producing bulk waste liquids and/or solids. The weight of a full bulk container can typically be below about 10 kg. The weight of an empty bulk container can typically be below about 0.5 kg, for example, about 0.2-0.3 kg. The term "bulk supply" can herein be used to indicate a large mass or volume of supply liquid or solid, for example, up to about 10 kg, from the same source, i.e. from the same bulk liquid supply container, which may be used in small amounts over several times. The term "bulk waste" can herein be used to indicate a large mass or volume of waste liquid or solid, for example, up to about 10 kg, being accumulated in the same waste container, by repetitive waste of small amounts of bulk solids and/or liquids. Examples of bulk supply liquids can be reagents, for example, auxiliary reagents, wash liquids, dilution liquids, system liquids, used, for example, to aspirate/dispense samples and/or reagents, and the like. Examples of bulk supply solids can be reaction vessels, secondary sample tubes for receiving aliquots of samples, disposable pipetting tips for aspirating/dispensing samples and/or reagents, sample and/or reagent and/or vessel and/or tip racks, tube holders, and the like. Examples of bulk waste liquids can be liquids used by the sample processing unit, which are not intended to be reused, for example, discarded samples, reagents, wash and system liquids, and mixtures thereof. Examples of bulk waste solids can be solids used by the sample processing unit, which are not intended to be reused, such as, for example, sample vessels, reaction vessels, reagent vessels, disposable tips used for processing samples.

The system can further comprise at least one weight measuring device. A "weight measuring device" can be a detector comprising a sensor for detecting the amount of bulk liquid or solid in a bulk container by measuring the weight of the bulk container and therefore indirectly also the volume or fill status. Thus the term "managing bulk liquids and/or bulk solids" can involve monitoring the fill status of one or more bulk containers by weight. According to one embodiment, it can involve also inventory management. This may comprise verification of the identity of inventory items, i.e. bulk containers, as well as their correct positioning, for example, by codes such as barcodes or RFID and/or by comparing expected weight values with measured values. In particular, the weight measuring device can comprise a loading plate, a reference base and a force measuring cell connected to the loading plate and to the reference base. The force measuring cell can comprise a vibrating wire sensor comprising a tensioned sensor wire. According to one embodiment, the force measuring cell can comprise a deformable frame having a sensor wire tensioned between two parts of the frame. The "loading plate" can be a plate, which can be biased with respect to the reference base as a function of the weight applied to it by a bulk container. In particular, the loading plate can be rigid compared to the force measurement cell and can transfer force to the force measuring cell when biased. More in particular, the force transferred to the force measurement cell can cause a deformation of the force measuring cell, for example, of the frame, and thereby a change in tension of the sensor wire. This can cause a change in vibrational frequency of the sensor wire, thereby resulting in an electric signal indicative of the weight of the bulk container. The term "wire" can encompass equivalents such as rod, string or the like which can be subjected to vibration or oscillation, for example, by a mechanical, electromagnetic or acoustical actuation when stretched between two points. Since this type of sensor can comprise only electromechanical parts, it can be more robust, more reproducible, more accurate and less influenced by environmental and handling factors, compared, for example, to other cheap and compact sensors such as strain gauges, which require the use of chemical parts such as adhesives.

The loading plate and the reference base can be resiliently coupled such that the loading plate can move towards or away from the reference base in the same direction of the force applied by the weight, i.e. by a bulk container to the loading plate. The loading plate and the reference base can typically be arranged substantially planar and parallel to each other. According to one embodiment, the loading plate can be arranged above the reference base and can receive a bulk container on its top such that the bulk container can exercise a push force on the loading plate in the direction of the reference base. In such a case, an increase in weight of the bulk container can correspond to an increase in push force applied to the loading plate, which can correspond to a decrease in distance between the loading plate and reference base, whereas a decrease in weight of the bulk container can correspond to a decrease in the push force applied to the loading plate and therefore to an increase of the distance between the loading plate and the reference plate. However, the loading plate may even be arranged below the reference base and can engage with a bulk container from below, for example, by a hook, fastener or the like, such that the bulk container can hang underneath and can exercise a pull force on the loading plate away from the reference base. In such a case, an increase in weight of the bulk container can correspond to an increase of pull force applied to the loading plate, which can correspond to an increase in distance between the loading plate and the reference base, whereas a decrease in weight of the bulk container can correspond to a decrease in force applied to the loading plate, which can correspond to a decrease in distance between the loading plate and the reference plate.

With such a construction of the weight measuring device, in which the force measurement cell can be arranged between the loading plate and the reference base and force applied to the loading plate can be transferred to the force measurement cell, a reduction in thickness, for example, about 4 cm or less between the loading plate and the reference plate, of the weight measuring device can be achieved compared to known weight measuring device based on the vibrating wire principle. This can make the weight measuring device more compact, which can be an advantage when installation space is limited.

According to one embodiment, the loading plate can move towards or away from the reference base in the same direction of the force applied by the weight and at the same time it can be laterally translatable in a direction substantially orthogonal to the direction of the applied force. According to such embodiment, an even further reduction in thickness, for example, about 2 cm or less between the loading plate and the reference plate, of the weight measuring device can be achieved. This can make the weight measuring device even more suitable for installation in the typically small space available in a bulk container compartment of a sample processing unit.

In the case in which the loading plate is arranged above the reference plate, an increase in force applied to the loading plate can correspond to a decrease in distance between the loading plate and reference base and to an increase in lateral displacement whereas a decrease in force applied to the loading plate can correspond to an increase of the distance and a decrease of the lateral displacement. In the case in which the loading plate is arranged below the reference plate, an increase in force applied to the loading plate can correspond to an increase in distance between the loading plate and the reference base and to a decrease in lateral displacement whereas a decrease in force applied to the loading plate can correspond to a decrease of the distance and an increase of the lateral displacement.

According to one embodiment, the weight measuring device can further comprise at least one tilt element and/or at least one translation element for defining the directions of movement of the loading plate with respect to the reference plate.

According to one embodiment, the loading plate and the reference plate can be directly coupled to each other, via, for example, protruding edges of the loading plate and/or of the reference base respectively. According to one embodiment, two opposite edges of the loading plate can protrude towards the reference base such as to engage with two respective edges of the reference base protruding towards the loading plate.

The force measuring cell can resiliently be coupled to the reference base and the loading plate such that deformation of the force measuring cell, caused by a varying force applied to the loading plate as the weight of the bulk container varies, can be reversible.

According to one embodiment, the system can comprise an electronic device electrically connected to at least one weight measuring device to receive the electric signals from at least one weight measuring device and to convert the electrical signals from analog into digital signals. In particular, the electronic device may be embodied as a common multiplexing device connected to a plurality of weight measuring devices.

According to one embodiment, each weight measuring device can comprise a non-volatile memory chip, such as, for example, an EEPROM, storing identification data related to the weight measuring device and/or to the force measuring cell. This can enable easy exchange, handling and calibration of the weight measuring device or force measuring cell. In particular, the weight measuring device may be embodied as a plug & play storing calibration data such as the sensor wire's characteristics, for example, typical vibrational frequency under standard conditions. Thus, when the system or controlling unit is started up and/or when a weight measuring device is replaced, the identity of the weight measuring device can automatically be determined, and calibration and/or compensation may be automatically executed without manual intervention.

According to one embodiment, the electronic device can receive identification data from the non-volatile memory chip and can confirm identity of the weight measuring device and/or calibrate the weight measuring device based on the identification data.

According to one embodiment, one or more weight measuring devices can be arranged in the bulk container unit, wherein the reference base of the weight measuring cell may be a surface of the bulk container unit or may be fixed, for example, removably fixed to a surface of the bulk container unit. According to one embodiment, one or more weight measuring devices can be arranged on a translatable drawer-like platform of the bulk container unit, so that loading and unloading of bulk container into/from the sample processing unit respectively can be facilitated.

According to one embodiment, one or more weight measuring devices can be arranged on a platform external to the sample processing unit, for example, on a bench-top or pavement surface.

According to one embodiment, the system can comprise a bulk container holder placeable onto the loading plate for holding a bulk container, the bulk container holder comprising an overflow chamber to receive bulk liquid eventually overflowing from the bulk container, thereby protecting the weight measuring device from the bulk liquid. The bulk container holder may engage with the loading plate such as to be securely held on the loading plate. In particular, the bulk container holder may be an adapter comprising for example one standard side loaded on a standard loading plate and one customizable side, for example, a recessed side to receive one or more bulk containers of different sizes or shapes. In this way, user guidance may be provided, thereby preventing wrong positioning and therefore measuring of the weight of the wrong bulk container.

According to one embodiment, the system can comprise a closure mechanism comprising a closure and a supply or waste pipe coupled to the closure such that at least part of the pipe can be in the bulk container for supplying bulk liquid from the bulk container or for wasting bulk liquid or solid into the bulk container when the bulk container is closed by the closure. The closure can prevent loss of bulk liquid from the bulk container and entry of foreign bodies into the bulk container.

According to one embodiment, the closure mechanism can comprise a closure sensor to detect closure of the bulk container and thereby the position of the pipe into the bulk container. According to one embodiment, the closure sensor can be an optical sensor such as, for example, a light sensor.

According to one embodiment, the closure can close the bulk container in a contactless manner or in a verging on manner. This can mean that the closure may just skim or skirt the bulk container, for example, the inner walls of a neck of an opening of the bulk container, with substantially forceless contact or low-force contact such that the measurement of the weight of the bulk container can be uninfluenced by the closure mechanism. The term "uninfluenced" herein can mean that the difference in the measured weight, in excess or defect due to the influence of the force applied to the bulk container by the closure mechanism can be less than about 50% of the weight of an empty bulk container.

According to one embodiment, the forceless or low-force contact can be achieved via a brush-like structure or flexible elastomeric material arranged around the pipe. This can be sufficient to achieve closure of the bulk container such as to prevent spilling of bulk liquid from the bulk container while keeping the pipe in place into the bulk container.

According to one embodiment, the system can comprise a controlling unit. The controlling unit may be embodied for example, as a programmable logic controller or software module running a computer-readable program provided with instructions to perform operations in accordance with a process operation plan. In particular, the controlling unit may be configured to receive the digital signals from the electronic device and transform the digital signals into one or more machine and/or user identifiable information data chosen from the group of presence or absence of a bulk container on a weight measuring device, empty status of a bulk container, full status of a bulk container, partially filled status of a bulk container, overloaded filled status of a bulk container, related to an amount of bulk liquid or solid in the bulk container.

According to one embodiment, the controlling unit can check whether a weight corresponding to the weight of an empty or partially filled bulk waste container can be placed on the loading plate or in the bulk container holder and/or check whether a weight corresponding to the weight of a full or partially filled bulk supply container can be placed on the loading plate or in the bulk container holder and can receive data from the closure sensor in order to determine whether the closure can close the bulk container before enabling waste of bulk liquid or solid into the bulk waste container or supply of bulk liquid or solid from the bulk supply container respectively.

For example, the controlling unit may be determine the presence of a bulk container, for example, an empty bulk waste container, by comparing the value of the weight of an empty bulk container with one or more reference values and/or by checking whether the closure is in the correct position.

The controlling unit may monitor in real time the fill volume status of one or more bulk containers and/or to monitor when threshold values can be reached.

The controlling unit may determine a difference in weight of a bulk liquid and/or bulk solid supply container between before and after supplying the sample processing unit with a bulk liquid and/or bulk solid respectively and/or a difference in weight of a bulk liquid and/or bulk solid waste container between before and after receiving a bulk liquid and/or bulk solid waste respectively from the sample processing unit. According to this embodiment, eventual leakage in a bulk container and/or signal drift can be more readily identified.

According to one embodiment, the controlling unit can disable waste of bulk liquid or solid into a bulk waste container when the weight of the bulk waste container reaches a predetermined value and/or can disable supply of bulk liquid or solid from a bulk supply container when the weight of the bulk supply container reaches a predetermined value. Alerts in the form of a user identifiable signal may also be generated when or before these threshold values are reached.

The controlling unit may redirect waste and/or supply of bulk liquid or solid into/from a different enabled bulk container respectively. In such a way, replacement of a full waste bulk container with an empty waste bulk container or replacement of an empty supply bulk container with a full supply bulk container may be enabled without interruption of the operation of the sample processing unit.

According to one embodiment, the controlling unit can communicate with a server or electronic inventory management unit and can provide and/or exchange inventory information and/or fill status information in order to trigger remote service and/or procurement of new supply bulk liquids and/or solids and/or disposal of waste bulk liquids and/or solids. The system can therefore also be well suitable for inventory management.

The same or a different controlling unit may be set up to control at least in part the workflow of the sample processing unit. For example it may control any one or more of the following operations: loading and/or wasting and/or washing of cuvettes and/or pipette tips, moving and/or opening of sample tubes and reagent cassettes, pipetting of samples and/or reagents, mixing of samples and/or reagents, washing pipetting needles or tips, washing mixing paddles, controlling of a light source, for example, selection of the wavelength, controlling a detector, collecting/comparing/assessing measurement data, moving cuvettes. In particular, the controlling unit may comprise a scheduler, for executing a sequence of steps within a predefined cycle time. The controlling unit may further determine the order of samples to be measured according to the assay type, urgency, and the like.

The various embodiments described in relation to the controlling unit may be applied also with other types of fill volume detectors and are therefore not necessarily limited to the use of a weight measuring device comprising a vibrating wire sensor.

Figure 1:
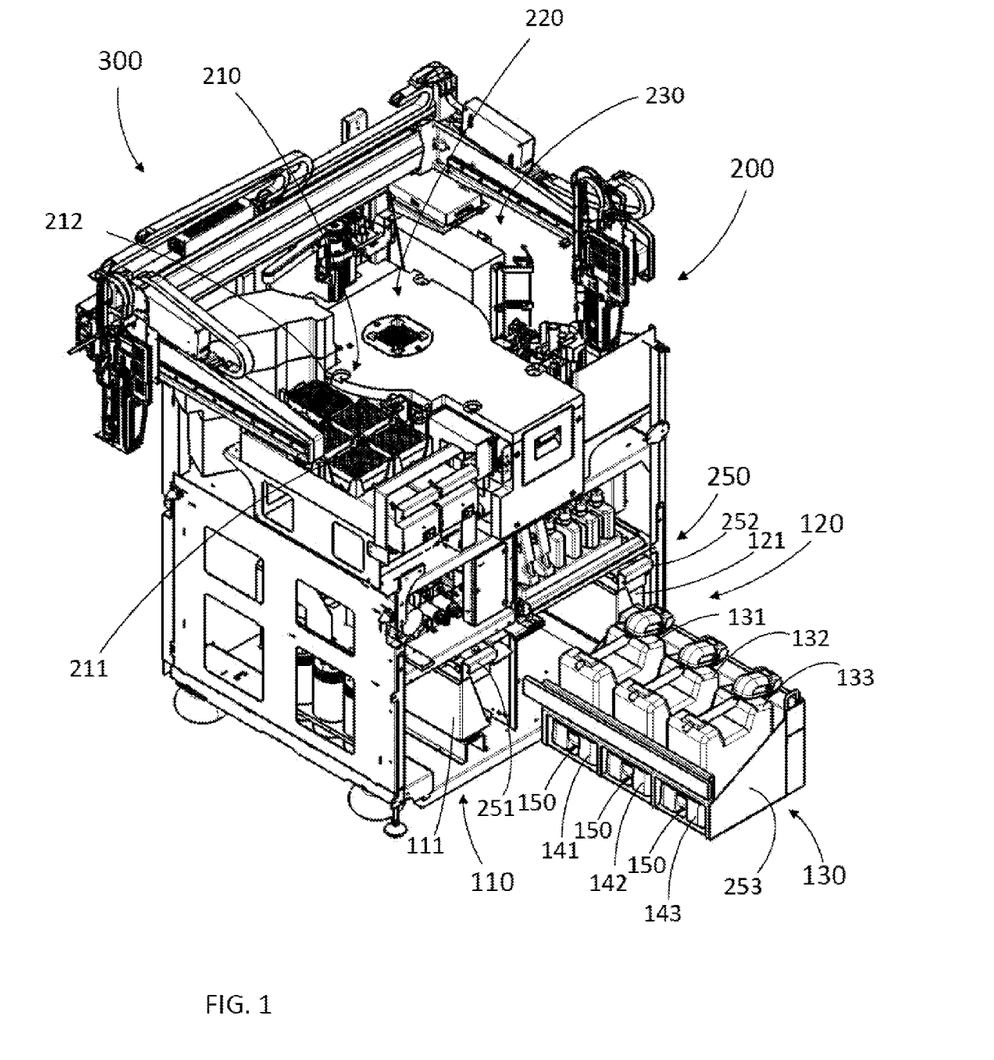
FIG. 1 illustrates a system for managing of bulk liquids and bulk solids for in-vitro diagnostics according to an embodiment of the present disclosure.

Referring initially to FIG. 1, a system 300 is shown for managing bulk liquids and bulk solids for in-vitro diagnostics. The system 300 can comprise a sample processing unit 200 (parts and housing removed for clarity). The sample processing unit 200 can in this case be an immunochemistry analyzer for carrying out immunodiagnostic tests. The sample processing unit 200 can comprise an area 210 for bulk solids, in this case disposable pipetting tips 211 and disposable reaction vessels 212. The sample processing unit 200 can further comprise a reaction section 220 for preparing reaction mixtures between samples and reagents while using the disposable pipetting tips 211 and the reaction vessels 212. The sample processing unit 200 can further comprise a detection module 230 for detecting the result of the reactions.

The system 300 can further comprise a first bulk container unit 110 comprising a first bulk solid waste container 111 for receiving the used disposable tips 211.

The system 300 can further comprise a second bulk container unit 120 comprising a second bulk solid waste container 121 for receiving the used reaction vessels 212 and eventually liquids contained therein.

The system 300 can further comprise a third bulk container unit 130 comprising bulk liquid supply containers 131, 132 for supplying wash and system liquids to the sample processing unit 200 and a bulk liquid waste container 133 for receiving bulk liquid waste from the sample processing unit 200. The bulk liquid containers 131, 132, 133 can be arranged in respective bulk container holder 141, 142, 143.

The system 300 can further comprise a weight measuring device 150 under each bulk container holder 141, 142, 143 and under each bulk waste container 111 and 121 (not visible in FIG. 1). The weight measuring devices 150 can be arranged on translatable drawer-like platforms 251, 252, 253 of a bulk container compartment 250 of the sample processing unit 200.

Figure 2:
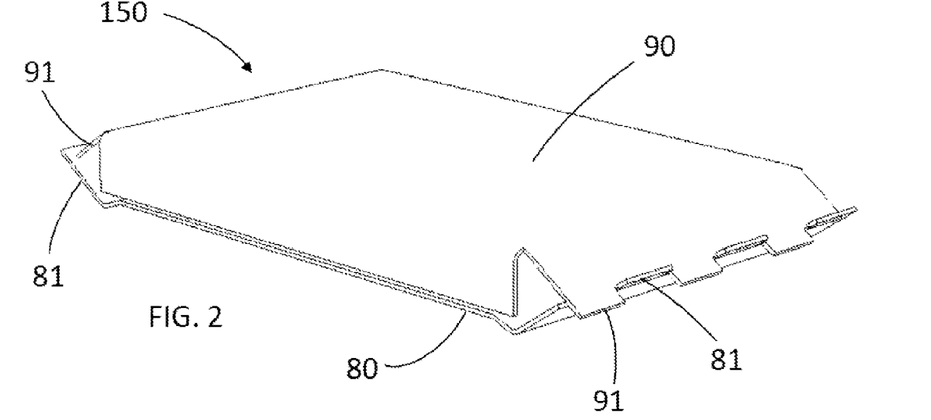
FIG. 2 illustrates a weight measuring device according to an embodiment of the present disclosure.

FIG. 2 shows a weight measuring device 150 (without electrical connections) according to one embodiment. The weight measuring device 150 can comprise a loading plate 90 and a reference base 80. The loading plate 90 and the reference plate 80 can be directly coupled to each other via protruding edges 91 of the loading plate 90 and protruding edges 81 of the reference base 80. In particular, two opposite edges 91 of the loading plate 90 can protrude towards the reference base 80 such as to engage with two respective edges 81 of the reference base 80 protruding towards the loading plate 90. The loading plate 90 can be arranged above the reference base 80 substantially parallel to the reference base 80 and can receive a bulk container (not shown) on its top such that the bulk container can exercise a push force on the loading plate 90 in the direction of the reference base 80. In such a case, an increase in weight of the bulk container can correspond to an increase in push force applied to the loading plate, causing the protruding edges 91, 81 to stretch and the distance between the loading plate and reference base to decrease. The loading plate 90 and reference base 80 may be made of metal, for example, steel or plastic, and can have resilient properties so that the protruding edges may return to their original position when the push force is removed from the loading plate 90. In particular, a decrease in weight of the bulk container can correspond to a decrease in the push force applied to the loading plate 90 and therefore to an increase of the distance between the loading plate 90 and the reference plate 80.

Figure 3:
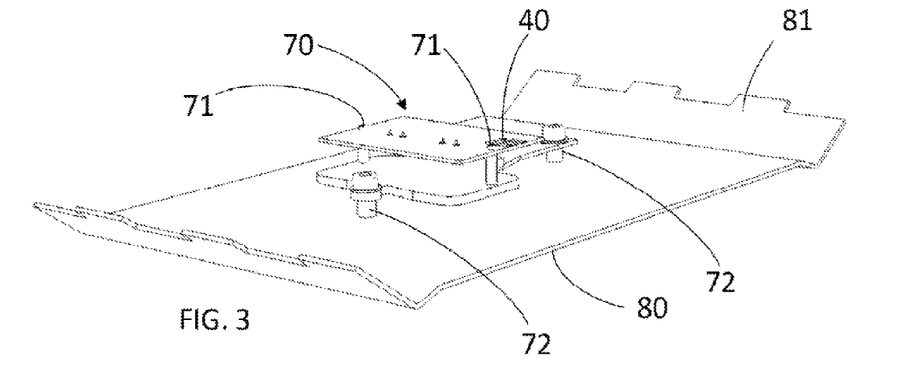
FIG. 3 illustrates details of the inside FIG. 2 according to an embodiment of the present disclosure.

FIG. 3 shows the inside of the weight measuring device 150 of FIG. 2 (loading plate 90 removed for clarity). The weight measuring device 150 can comprise a force measuring cell 70 (parts removed for clarity) connected to the loading plate 90 via connectors 71 and to the reference base 80 via connectors 72.

Figure 4:
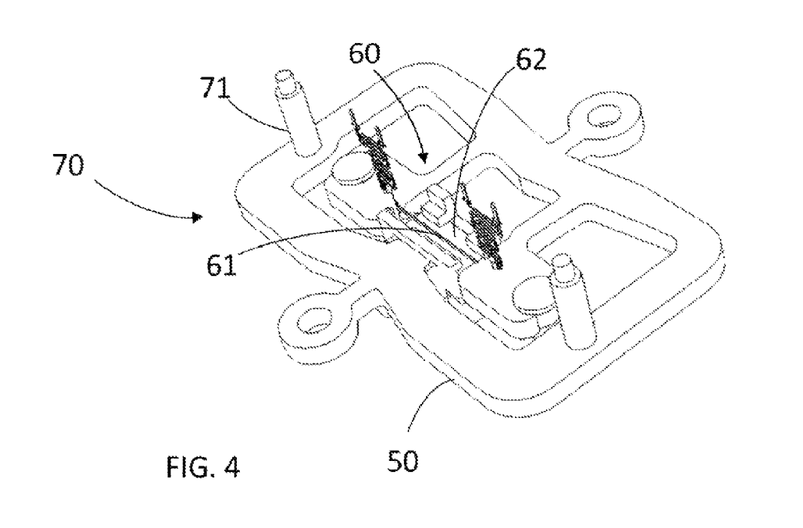
FIG. 4 illustrates details of a force measuring cell according to an embodiment of the present disclosure.

FIG. 4 shows parts of the force measurement cell 70 in more detail. In particular, the force measuring cell 70 can comprise a vibrating wire sensor 60 comprising a sensor wire 61 tensioned between two parts of a deformable frame 50 and arranged in the magnetic field of a permanent magnet 62 (shown in part). The sensor wire 61 can be subjected to electric actuation, for example, when switching the weight measuring device 150 on. This can induce vibration to the sensor wire 61, which can be maintained at a certain vibrational frequency by the magnetic field, dependent on the characteristics of the sensor wire 61, such as dimensions and material, of the magnetic field and of the tension of the sensor wire 61. A force applied to the loading plate 90 can cause a change in the distance between the loading plate 90 and the reference base 80. The force can be transferred to the force measuring cell 70, via connectors 71 and connectors 72 which can be rigid compared to the frame 50. This can cause a deformation of the frame 50. Deformation of the frame 50 can cause in turn a change in tension of the sensor wire 61 and therefore a change in vibrational frequency of the sensor wire 61. The vibrational frequency can be transformed into an electric signal indicative of the weight of the bulk container.

The weight measuring device 150 can further comprise a non-volatile memory chip 40 storing identification data related to the weight measuring device 150 and to the force measuring cell 70, such as, for example, the sensor wire's characteristics and calibration data. This can enable easy exchange, handling and calibration of the weight measuring device 150.

The force measuring cell 70 can be resiliently coupled to the reference base 80 and to the loading plate 90 such that deformation of the force measuring cell 70, and in particular of the frame 50 caused by a force applied to the loading plate 90 can be reversible as the weight of the bulk container varies.

Figure 5:
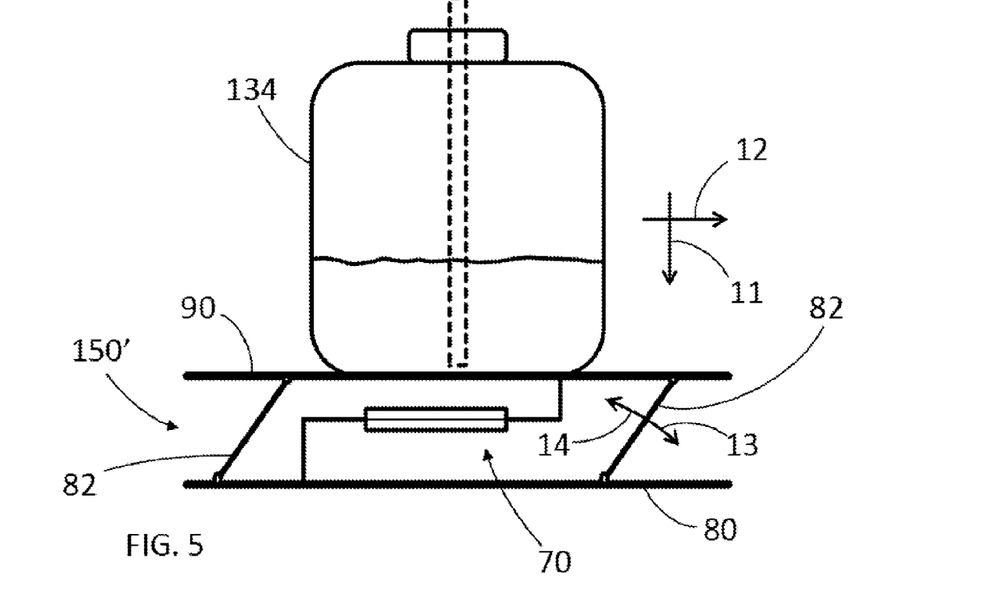
FIG. 5 illustrates schematically the weight measurement device according to another embodiment of the present disclosure.

FIG. 5 shows schematically a weight measurement device 150', which is a variation of the weight measuring device 150 of FIGS. 2-4. In particular, the difference with the weight measuring device 150 of FIGS. 2-4 is that the loading plate 90 of the weight measuring device 150' can move towards the reference base 80 in the direction 11 of the force applied by a bulk container 134 placed onto the loading plate 90 and can further be laterally translatable in a direction 12 substantially orthogonal to the direction of the applied force. In particular, an increase in force applied to the loading plate 90 can correspond to a decrease in distance between the loading plate 90 and reference base 80 and to an increase in lateral displacement whereas a decrease in force applied to the loading plate 90 can correspond to an increase of the distance between loading plate 90 and reference base 80 and a decrease of the lateral displacement. The boundaries of movement can be defined by tilt elements 82, which can be resiliently coupled to the loading plate 90 and reference plate 80 such as to reversibly tilt in a downward 13 or upward 14 direction depending on the force applied to the loading plate 90.

Figure 6:
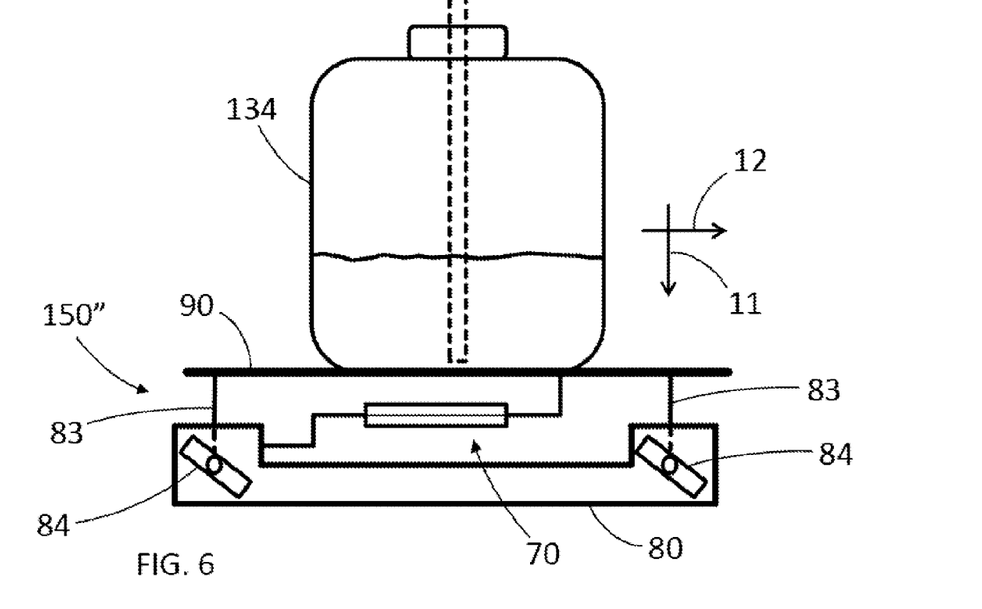
FIG. 6 illustrates schematically the weight measurement device according to a further embodiment of the present disclosure.

FIG. 6 shows schematically a weight measurement device 150", which is a variation of the weight measuring device 150' of FIG. 5. In particular, the difference with the weight measuring device 150' of FIG. 5 is that the boundaries of movement can be defined by translation elements 83 instead of tilt elements 82. The translation elements 83 can be fixedly coupled to the loading plate 90 and can fit in guiding supports 84 of the reference base 80, into which they may slide or roll, in a way which substantially can achieve the same effect as tilt elements 82.

Figure 7:
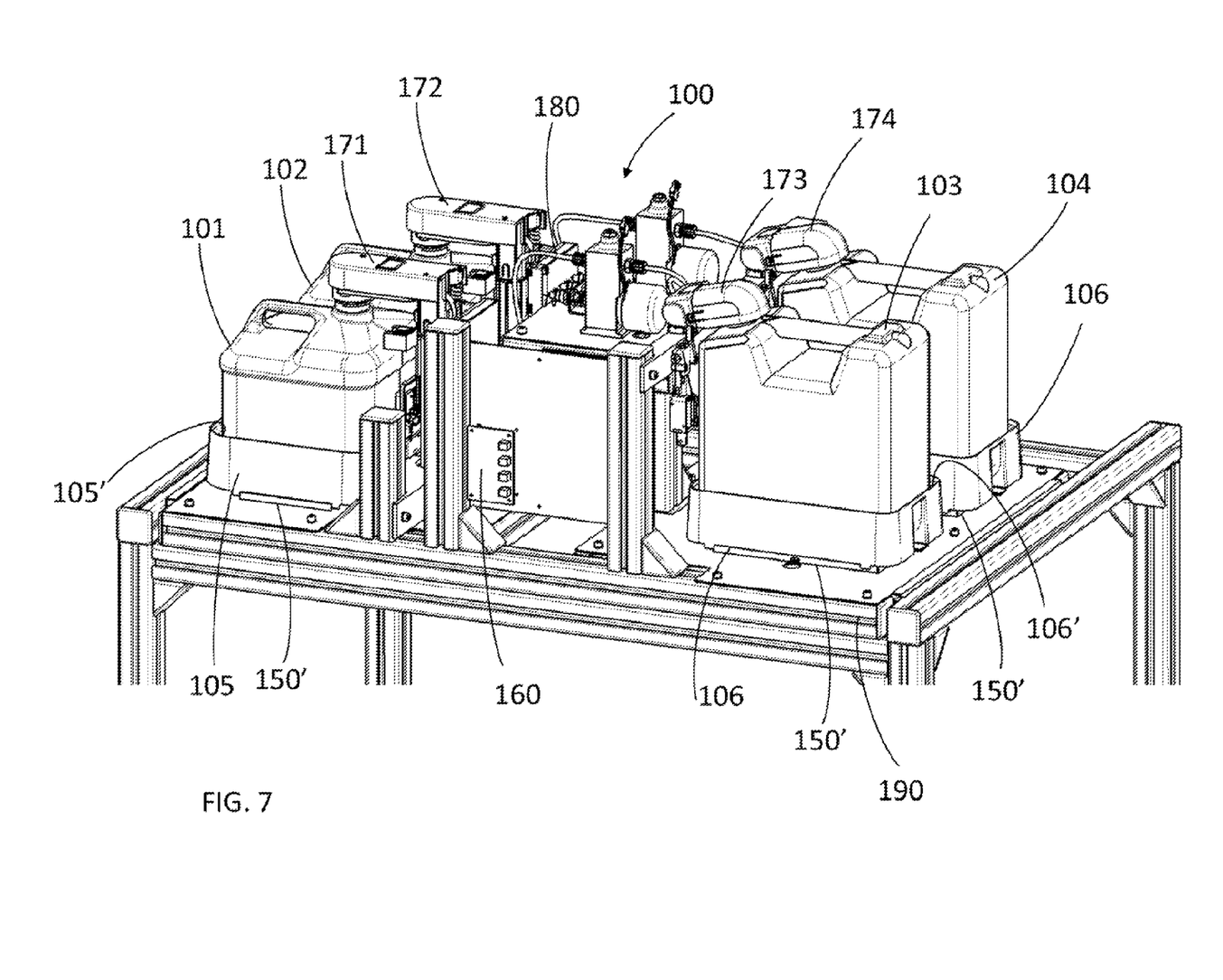
FIG. 7 illustrates of bulk container unit according to an embodiment of the present disclosure.

FIG. 7 shows an example of bulk container unit 100 external to a sample processing unit such as that of FIG. 1. The bulk container unit 100 can comprise two bulk supply containers 101, 102 and two bulk liquid waste containers 103, 104 arranged in respective bulk container holders 105, 106. The bulk container unit 100 can further comprise under each bulk container holder 105, 106 a weight measuring device 150' of the type shown in FIG. 5 arranged on a platform 190. The weight measuring devices 150' can have a height of about 2 cm.

The bulk container holders 105, 106 can comprise overflow chambers 105', 106' to receive bulk liquids eventually overflowing from the bulk containers 101, 102, 103, 104, thereby protecting the weight measuring devices 150' from the bulk liquids.

The bulk container unit 100 can further comprise an electronic device 160 electrically connected to the weight measuring devices 150' to receive electric signals from the weight measuring devices 150' and to convert the electrical signals from analog into digital signals.

The bulk container unit 100 can comprise a closure mechanism 171, 172, 173, 174 for each bulk container 101, 102, 103, 104 respectively.

Figure 8:
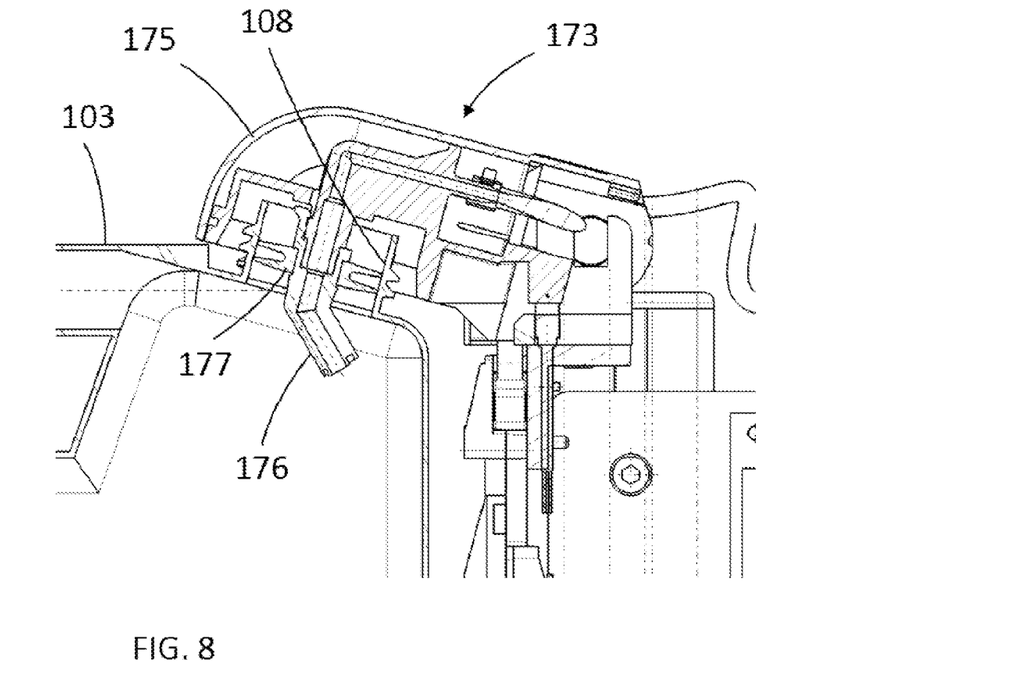
FIG. 8 illustrates a closure mechanism in cross section according to an embodiment of the present disclosure.
Figure 9:
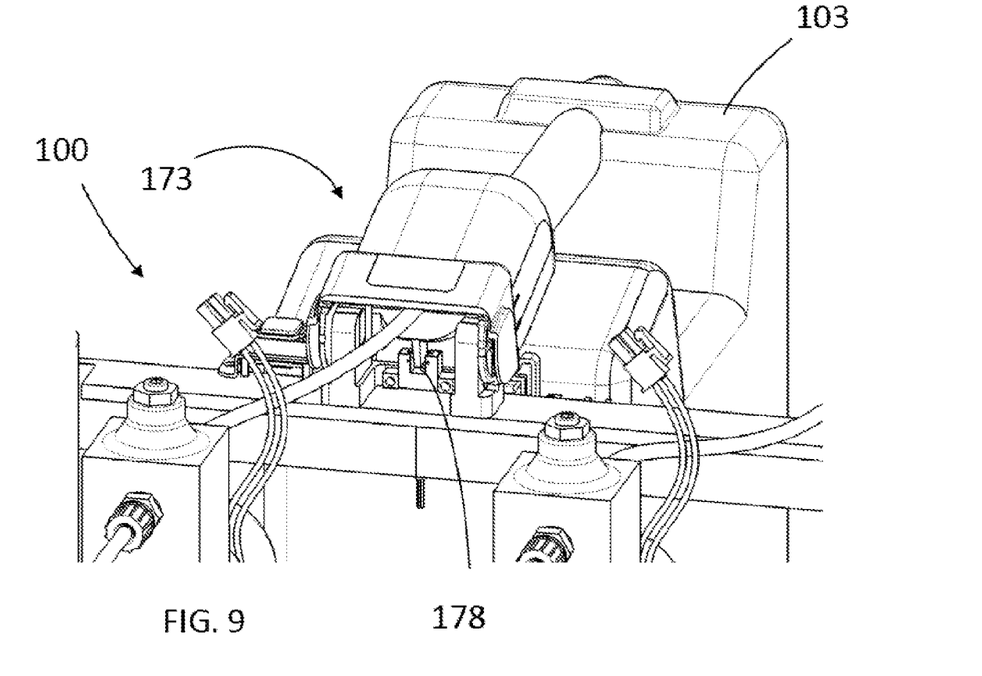
FIG. 9 illustrates the same closure mechanism of FIG. 8 from a different perspective according to an embodiment of the present disclosure.
Figure 10:
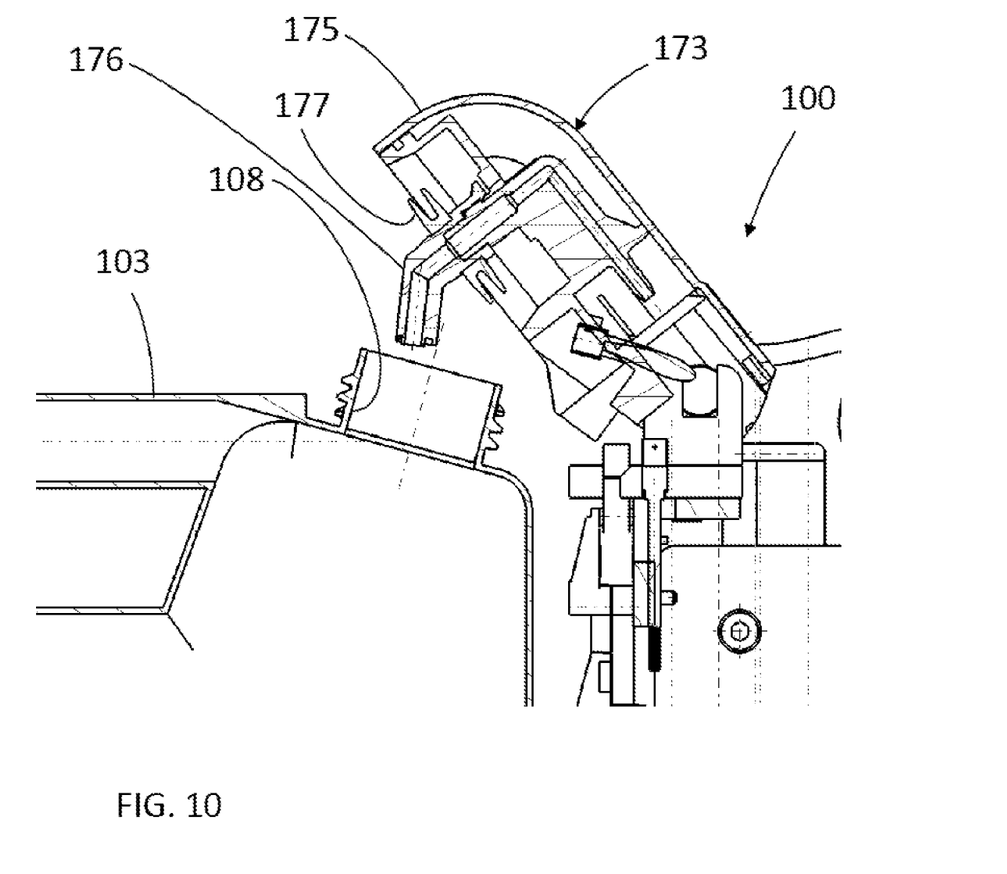
FIG. 10 illustrates the same closure mechanism of FIGS. 8 and 9 in an open status according to an embodiment of the present disclosure.

FIGS. 8, 9 and 10 show further details of the closure mechanism 173 of the bulk liquid waste container 103, for example. In particular, the closure mechanism 173 can comprise a closure 175 and a waste pipe 176 coupled to the closure 175 such that a part of the pipe 176 can be in the bulk container 103 for wasting bulk liquid into the bulk liquid container 103 when the bulk container 103 is closed by the closure 175. The closure 175 can be external to the bulk container 103 and can be pivotally arranged in the bulk container unit 100 such as to close the bulk container 103 when it is pivoted downwards (FIGS. 8 and 9) and to open the bulk container 103 when it is pivoted upwards (FIG. 10). In particular, the closure mechanism 173 can close the bulk container 103 in a verging on manner with substantially forceless contact such that the measure of the weight of the bulk container 103 can be uninfluenced by the closure mechanism 173. This can be achieved by a flexible elastomeric material 177 arranged around the pipe 176 such as to just skim the inner walls 108 of the opening of the bulk container 103. This can be sufficient to achieve closure of the bulk container 103 such as to prevent spilling of bulk liquid from the bulk container while keeping the pipe 176 in place into the bulk container 103.

The closure mechanism 173 can also comprise a light sensor 178 (FIG. 9) to detect closure of the bulk container 103 and thereby the position of the pipe 176 into the bulk container 103.

The bulk container unit 100 can further comprise a controlling unit or software module 180. The controlling unit 180 can receive the digital signals from the electronic device 160 and transform the digital signals into one or more machine and/or user identifiable information data chosen from the group of presence or absence of a bulk container 101, 102, 103, 104 on a respective weight measuring device 150', empty status of a bulk container 101, 102, 103, 104, full status of a bulk container 101, 102, 103, 104, partially filled status of a bulk container 101, 102, 103, 104, overloaded filled status of a bulk container 101, 102, 103, 104, related to an amount of bulk liquid in the bulk container 101, 102, 103, 104.

The controlling unit 180 can also receive identification data from the non-volatile memory chips 40 (not shown in FIG. 7) of the weight measuring devices 150' and can confirm identity of the weight measuring devices 150' and/or calibrate the weight measuring device 150' based on the identification data.

More in particular, the controlling unit 180 can check whether a weight corresponding to the weight of an empty or partially filled bulk liquid waste container 103, 104 can be placed in the respective bulk container holder 106 on the respective weight measuring device 150' and can check whether a weight corresponding to the weight of a full or partially filled bulk liquid supply container 101, 102 can be placed on in the respective bulk container holder 105. The controlling unit 180 can further receive data from the closure sensors 178 in order to determine whether the closure mechanisms 171, 172, 173, 174 can close the respective bulk containers 101, 102, 103, 104 before enabling waste of bulk liquid into the bulk liquid waste containers 103, 104 or supply of bulk liquids from the bulk liquid supply containers 101, 102 respectively.

The controlling unit 180 can further disable waste of bulk liquid into the bulk liquid waste container 103 when the weight of the bulk liquid waste container 103 reaches a predetermined value and can redirect waste of bulk liquid into the other bulk liquid waste container 104.

The controlling unit 180 can further disable supply of bulk liquid from the bulk liquid supply container 101 when the weight of the bulk liquid supply container 101 reaches a predetermined value and to redirect supply of bulk liquid from the other bulk liquid container 102.

The bulk container unit 100 and therefore the system 300 can therefore be operated continuously without interruption and can enable continuous loading/unloading of bulk containers.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A system for managing bulk liquids and/or bulk solids for in-vitro diagnostics, the system comprising:
    a sample processing unit;
    at least one bulk container unit for receiving at least one bulk liquid and/or bulk solid supply container for supplying the sample processing unit with at least one bulk liquid and/or bulk solid respectively and/or at least one bulk liquid and/or at least one bulk solid waste container for receiving at least one bulk liquid and/or bulk solid waste respectively from the sample processing unit;
    at least one weight measuring device comprising a loading plate, a reference base and a force measuring cell connected to the loading plate and to the reference base, the force measuring cell comprising a vibrating wire sensor comprising a tensioned sensor wire, wherein the loading plate is biased with respect to the reference base by a weight applied to the loading plate by a bulk container and to transfer force to the force measuring cell, the transferred force causing a deformation of the force measuring cell and a change in tension of the sensor wire causing a change in vibrational frequency resulting in an electric signal indicative of the weight of the bulk container,
    wherein the loading plate and the reference base are resiliently coupled such that the loading plate is movable towards or away from the reference base in the same direction of the force applied by the weight to the loading plate and at the same time it is laterally translatable in a direction orthogonal to the direction of the applied force, wherein an increase in force applied to the loading plate corresponds to a decrease in distance between the loading plate and reference base and to an increase in lateral displacement and wherein a decrease in force applied to the loading plate corresponds to an increase of the distance and a decrease of the lateral displacement.

2. The system according to claim 1, wherein the weight measuring device further comprises at least one tilt element and/or at least one translation element for defining the directions of movement of the loading plate with respect to the reference plate.

3. The system according to claim 1, wherein the weight measuring device comprises a non-volatile memory chip storing identification data related to the weight measuring device and/or to the force measuring cell.

4. The system according to claim 3, wherein the electronic device receives identification data from the non-volatile memory chip and confirms identity of the weight measuring device and/or calibrates the weight measuring device based on the identification data.

5. The system according to claim 1, wherein the weight measuring device is arranged on a platform of a bulk container compartment of the sample processing unit or on a platform external to the sample processing unit.

6. The system according to claim 1, further comprising,
a bulk container holder placeable onto the loading plate for holding a bulk container, the bulk container holder comprising an overflow chamber to receive bulk liquid eventually overflowing from the bulk container, thereby protecting the weight measuring device from the bulk liquid.

7. The system according to claim 1, wherein the bulk container unit comprises a closure mechanism comprising a closure and a supply or waste pipe coupled to the closure such that at least part of the pipe is in the bulk container for supplying bulk liquid from the bulk container, or for wasting bulk liquid or solid into the bulk container, when the bulk container is closed by the closure.

8. The system according to claim 7, wherein the closure mechanism comprises a closure sensor to detect closure of the bulk container and the position of the pipe in the bulk container.

9. The system according to claim 8, wherein the closure closes the bulk container in a contactless or verging on manner with forceless contact or low-force contact such that measure of the weight of the bulk container is uninfluenced by the closure mechanism.

10. The system according to claim 9, wherein the closure mechanism comprises flexible elastomeric material arranged around the pipe and achieves closure of the bulk container such as to prevent spilling of bulk liquid from the bulk container while keeping the pipe in place into the bulk container.

11. The system according to claim 1, further comprising,
an electronic device electrically connected to at least one weight measuring device to receive the electric signals from at least one weight measuring device and to convert the electrical signals from analog into digital signals.

12. The system according to claim 11, further comprising,
a controlling unit to receive the digital signals from the electronic device and to transform the digital signals into one or more machine and/or user identifiable information data chosen from the group of presence or absence of a bulk container on a weight measuring device, empty status of a bulk container, full status of a bulk container, partially filled status of a bulk container, overloaded filled status of a bulk container, related to an amount of bulk liquid, solid in the bulk container or combinations thereof.

13. The system according to claim 12, wherein the controlling unit checks whether a weight corresponding to the weight of an empty or partially filled bulk waste container is placed on the loading plate or in the bulk container holder and/or checks whether a weight corresponding to the weight of a full or partially filled bulk supply container is placed on the loading plate or in the bulk container holder and receives data from the closure sensor in order to determine whether the closure closes the bulk container before enabling waste of bulk liquid or solid into the bulk waste container or supply of bulk liquid or solid from the bulk supply container respectively.

14. The system according to claim 12, wherein the controlling unit disables waste of bulk liquid or solid into a bulk waste container when the weight of the bulk waste container reaches a predetermined value and/or disables supply of bulk liquid or solid from a bulk supply container when the weight of the bulk supply container reaches a predetermined value and redirects waste and/or supply of bulk liquid or solid into/from a different enabled bulk container respectively.

15. The system according to claim 12, wherein the controlling unit determines a difference in weight of a bulk liquid and/or bulk solid supply container between before and after supplying the sample processing unit with a bulk liquid and/or bulk solid respectively and/or a difference in weight of a bulk liquid and/or bulk solid waste container between before and after receiving a bulk liquid and/or bulk solid waste respectively from the sample processing unit.

* * * * *